United States Patent
Giles

(10) Patent No.: US 10,481,048 B2
(45) Date of Patent: Nov. 19, 2019

(54) SOIL SAMPLING COLLECTION SYSTEM AND METHOD OF USE

(71) Applicant: Michael Shane Giles, Cordova, TN (US)

(72) Inventor: Michael Shane Giles, Cordova, TN (US)

( * ) Notice: Subject to any disclaimer, the term of this patent is extended or adjusted under 35 U.S.C. 154(b) by 0 days.

(21) Appl. No.: 15/268,461

(22) Filed: Sep. 16, 2016

(65) Prior Publication Data

US 2017/0191905 A1      Jul. 6, 2017

Related U.S. Application Data

(60) Provisional application No. 62/219,326, filed on Sep. 16, 2015.

(51) Int. Cl.
   *G01N 1/08*        (2006.01)
   *G01N 33/24*       (2006.01)
   *A01B 79/00*       (2006.01)

(52) U.S. Cl.
   CPC .............. *G01N 1/08* (2013.01); *A01B 79/00* (2013.01); *G01N 33/24* (2013.01); *G01N 2001/085* (2013.01); *G01N 2033/245* (2013.01)

(58) Field of Classification Search
   CPC ..... G01N 1/08; G01N 2033/245; A01B 79/00
   USPC ..... 73/864.31; 111/149, 157, 159, 162, 163, 111/171; 37/93, 96, 242, 244, 415
   See application file for complete search history.

(56) References Cited

U.S. PATENT DOCUMENTS

| | | | | |
|---|---|---|---|---|
| 4,356,734 A | * | 11/1982 | Ivancsics | G01N 1/04 172/438 |
| 5,490,339 A | * | 2/1996 | Accettola | E02F 3/181 299/39.2 |
| 2009/0071714 A1 | * | 3/2009 | Shrestha | A01C 21/002 175/20 |

FOREIGN PATENT DOCUMENTS

| | | | | |
|---|---|---|---|---|
| GB | 2482261 A | * | 1/2012 | E02F 3/20 |
| WO | WO 2007034245 A1 | * | 3/2007 | E01H 12/00 |

* cited by examiner

*Primary Examiner* — Harshad R Patel
(74) *Attorney, Agent, or Firm* — Baker Donelson

(57) ABSTRACT

A soil sampling collection system is disclosed. In one embodiment, a soil sampling collection system comprises a blade mounted on the front of the utility vehicle. The utility vehicle is powered to move through a designated area and configured to automatically collect soil samples as the system moves through the designated area. The blade is configured to move up and down via power hydraulics. A blade guard is mounted to the blade. A soil collection reservoir mounted on or near the back of the blade guard. A conveyor is mounted in between the soil collection reservoir and the front of the vehicle. The conveyor comprises a plurality of soil bags or cups configured to receive individual soil samples from the soil collection reservoir. A method for collecting soil samples is also disclosed.

3 Claims, 9 Drawing Sheets

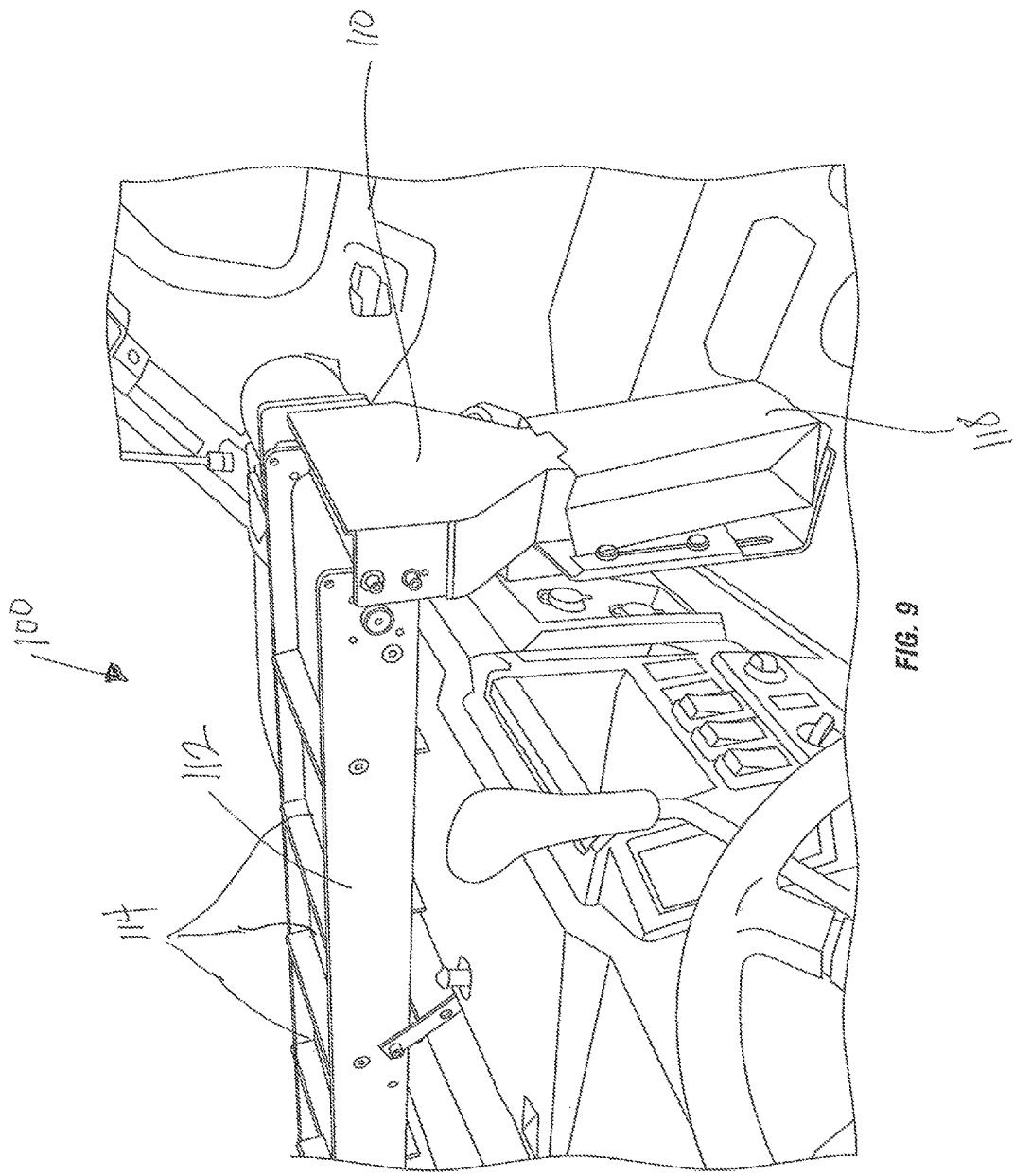

SOIL SAMPLING COLLECTION SYSTEM AND METHOD OF USE

FIELD

This technology relates generally to a soil sampling collection system and method of use applicable to the precision agricultural industry. More particularly, this technology relates to an automatic soil sampling collection system and method of use, wherein the collection system is powered to move through a field, or other designated area, and wherein the collection system is configured to automatically collect soil samples as the system moves through the field.

BACKGROUND

Precision agriculture or precision farming is a farming management concept based on observing, measuring and responding to intra and inter-field variability in crops. Precision agriculture strives to optimize field-level management with regarding to crop science, environmental protection and economics. Regarding crop science, precision agriculture allows farmers to match farming practices more closely to crop needs. Regarding environmental protection, precision agriculture allows the reduction of environmental risks and footprint of farming. And, regarding economics, precision agriculture boosts competitiveness through efficient practices.

Precision agriculture provides farmers with information that allows farmers, among other things, to enhance the quality of their farm products, to build up a record of their individual farm; to improve decision-making pertaining to location and variety of crops planted; and to foster greater traceability.

Precision agriculture is a four-stage process using techniques to observe spatial variability including (1) geolocation of data or geolocating a field, (2) characterizing intra and inter-field variability, (3) decision making, and (4) implementing practices to address variability. Stage two, characterizing intra and inter-field variability, may result from a number of factors including climatic conditions, soils, cropping practices, weeds and disease. Numerous soil samples are collected and tested to determine texture, depth and nitrogen levels of the soil, and such information is used by farmers to determine location and type of crop to be planted on each field.

Soil samples are generally collected with a hand probe and bucket, a time consuming process. Also, other forms of automated soil sampling devices are in use, however, all utilize the probe concept.

There is a need for an automatic, continuous soil sampling collection system and method of use, which facilitates the effective and efficient collection of numerous soil samples.

DESCRIPTION OF THE FIGURES

FIG. 9 is a perspective view of the components of a soil sampling collection system according to FIG. 8.

DETAILED DESCRIPTION

Figure 7:
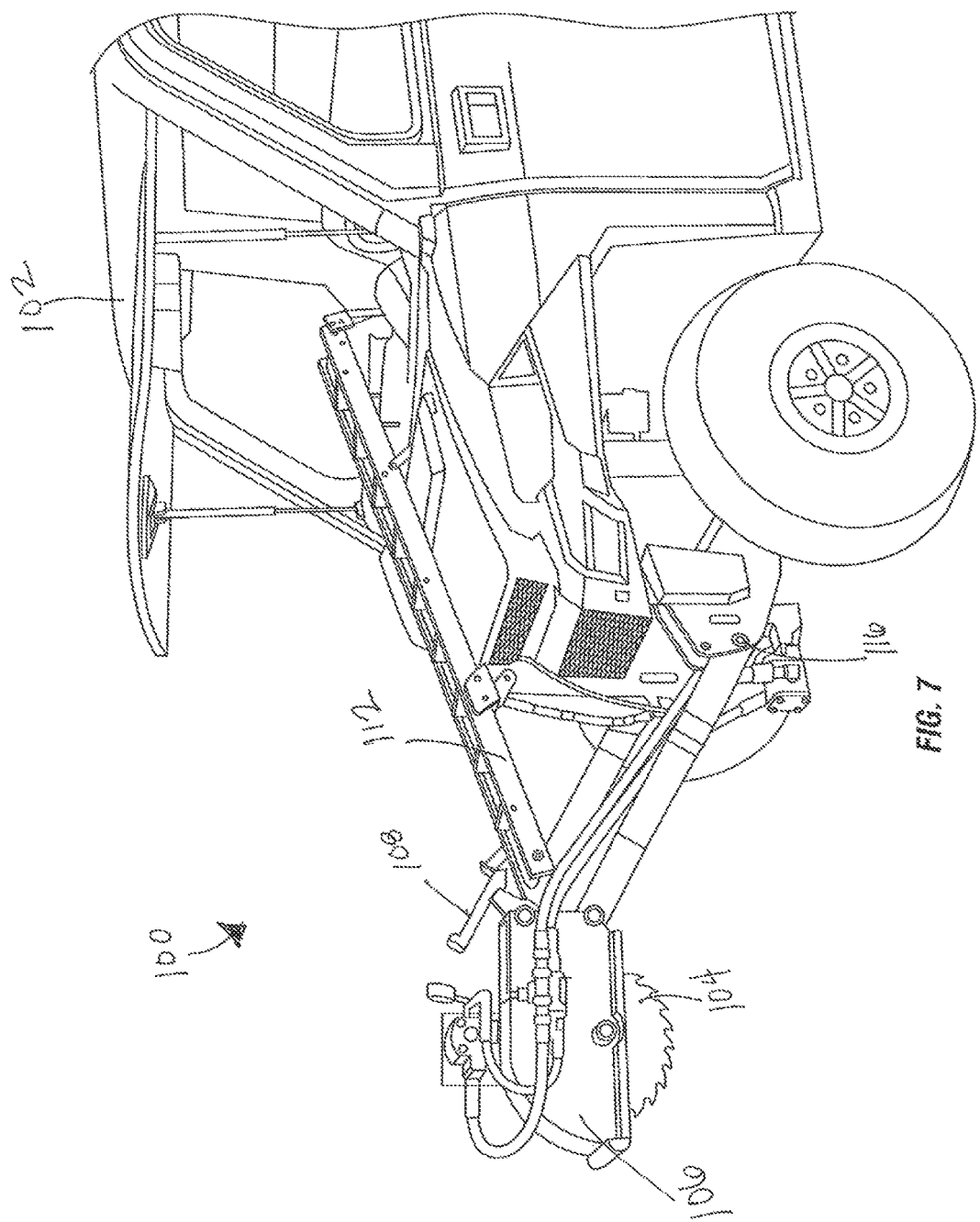
FIG. 7 is a perspective view of the components of a soil sampling collection system according to another example embodiment.

An automatic, continuous soil sampling collection system 100 and method is disclosed. In one embodiment, the soil sampling system 100 disclosed is collected outside the cab of the vehicle 102 which prevents dust from entering the cab. In another embodiment, the soil sampling system 100 may involve the conveyor 112 entering the cab as shown in FIG. 7. Additionally, the soil sampling system 100 allows the soil to be collected in one continuous movement. While collecting soil samples, the vehicle may slow down but keeps moving allowing soil samples to be gathered in one continuous movement.

Referring to FIGS. 1 to 9, in one embodiment, the soil sampling system 100 comprises a blade 104, such as a saw blade, mounted on the utility vehicle 102 or all-terrain vehicle. The utility vehicle or all-terrain vehicle may be powered to move through a field, or other designated area, and may be configured to automatically collect soil samples as the system moves through the field. In one embodiment, the blade 104 is attached to the utility vehicle at 116 (see FIG. 4) and moves up and down via power hydraulics.

Figure 8:
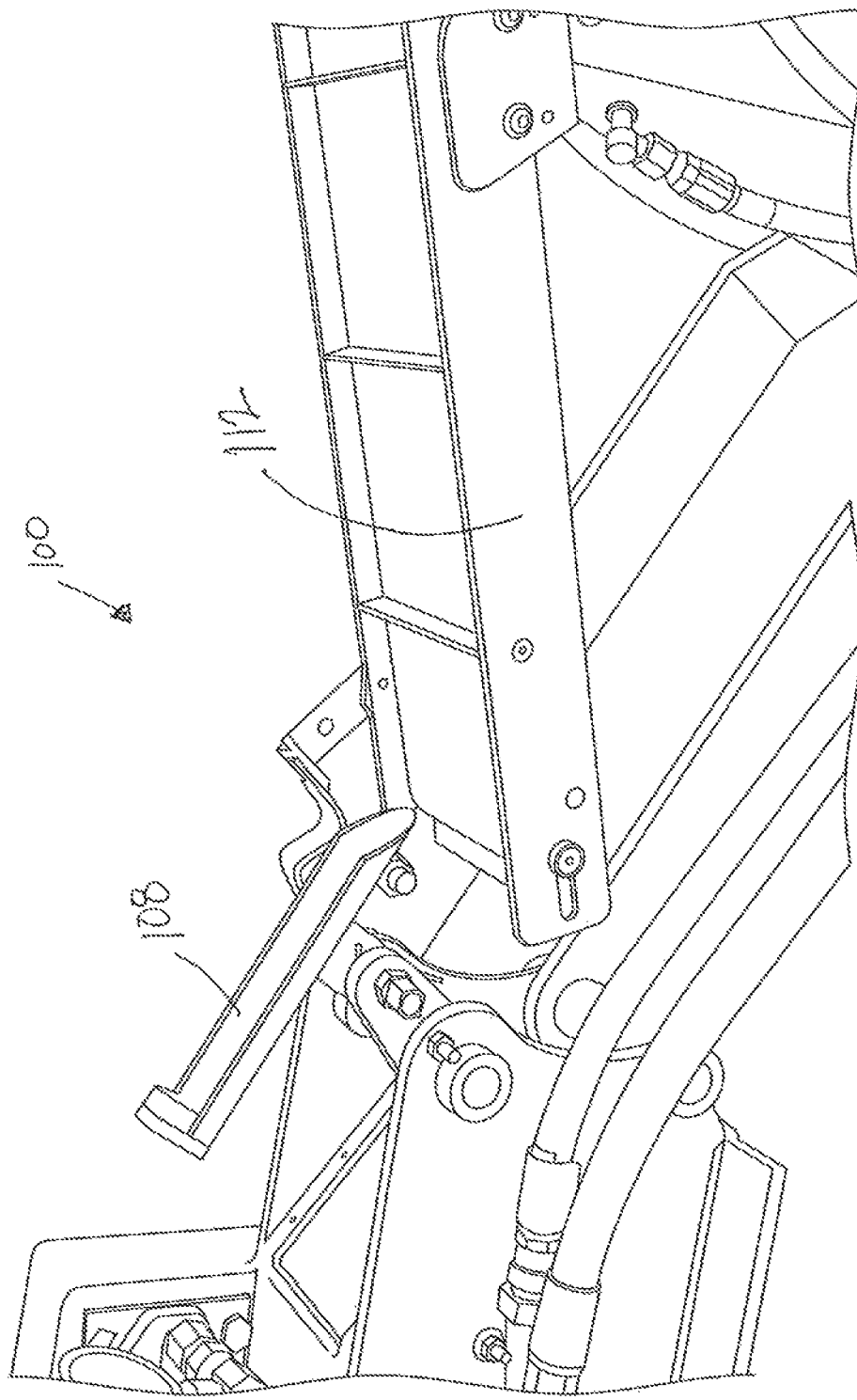
FIG. 8 is a perspective view of the components of a soil sampling collection system according to a further example embodiment.

In one embodiment, a blade guard 106 may be mounted to the blade 104. A soil collection reservoir 108 or spout may be attached or mounted on or near the back of the blade guard 106. Referring to FIGS. 7-9, in one embodiment, the system 100 comprises a conveyor 112 having a plurality of soil receiving apparatuses 114 (or cups or any other soil receiving apparatus) assembled around the perimeter of the conveyer 112. The conveyor 112 is mounted in between the soil collection reservoir 108 and the front of the vehicle 102. Each soil bag 114 on the conveyer 112 is configured to receive individual soil samples from the soil collection reservoir 108 or spout and into a designated soil bag when the blade 104 is moved upward, away from the ground. In one embodiment, a funnel 110 may be used to assist with the transfer of the soil sample from the reservoir 108 to the soil bag 114 on the conveyor 112.

Figure 1:
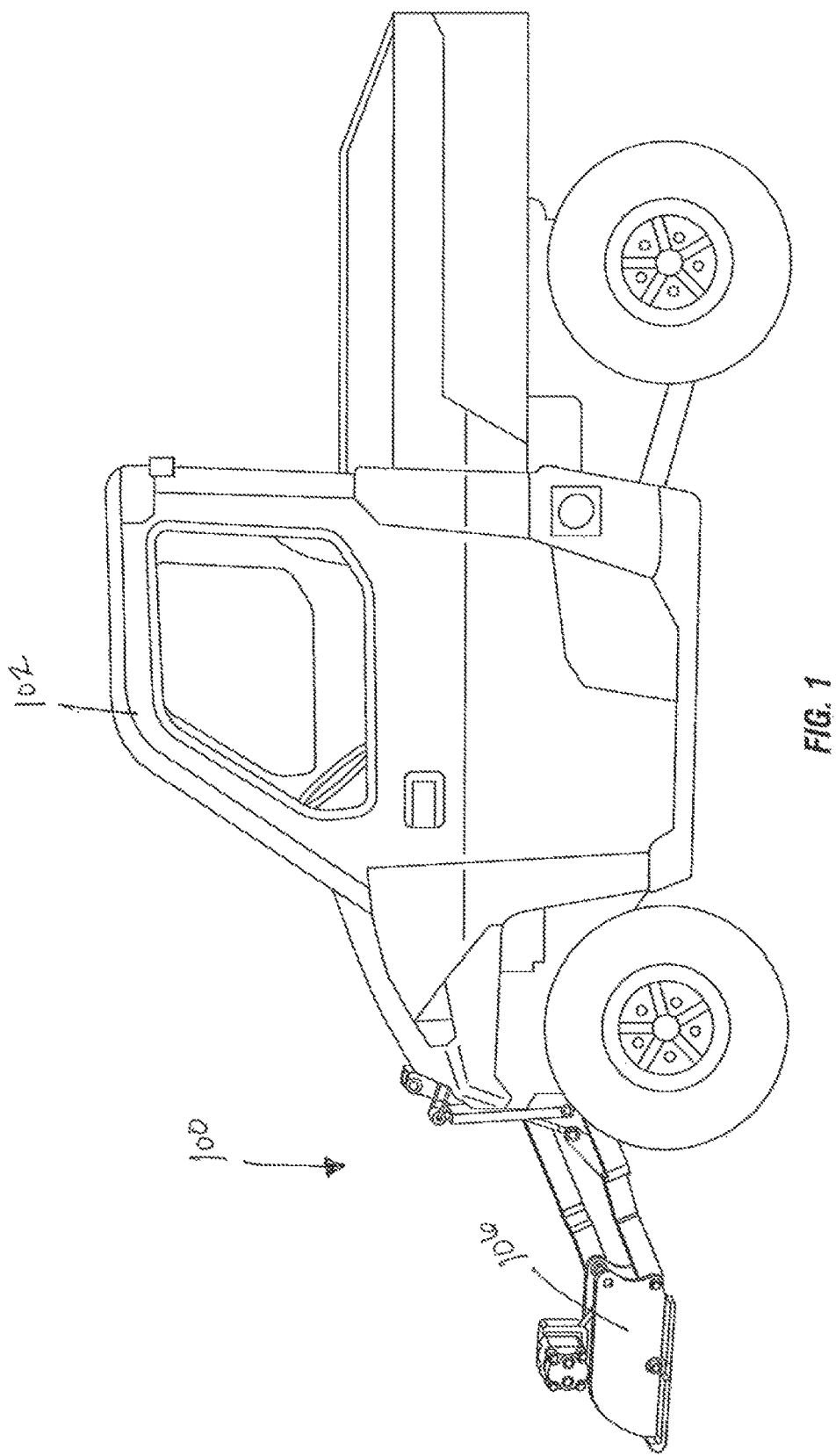
FIG. 1 is a side perspective view of a soil sampling collection system according to one example embodiment.
Figure 2:
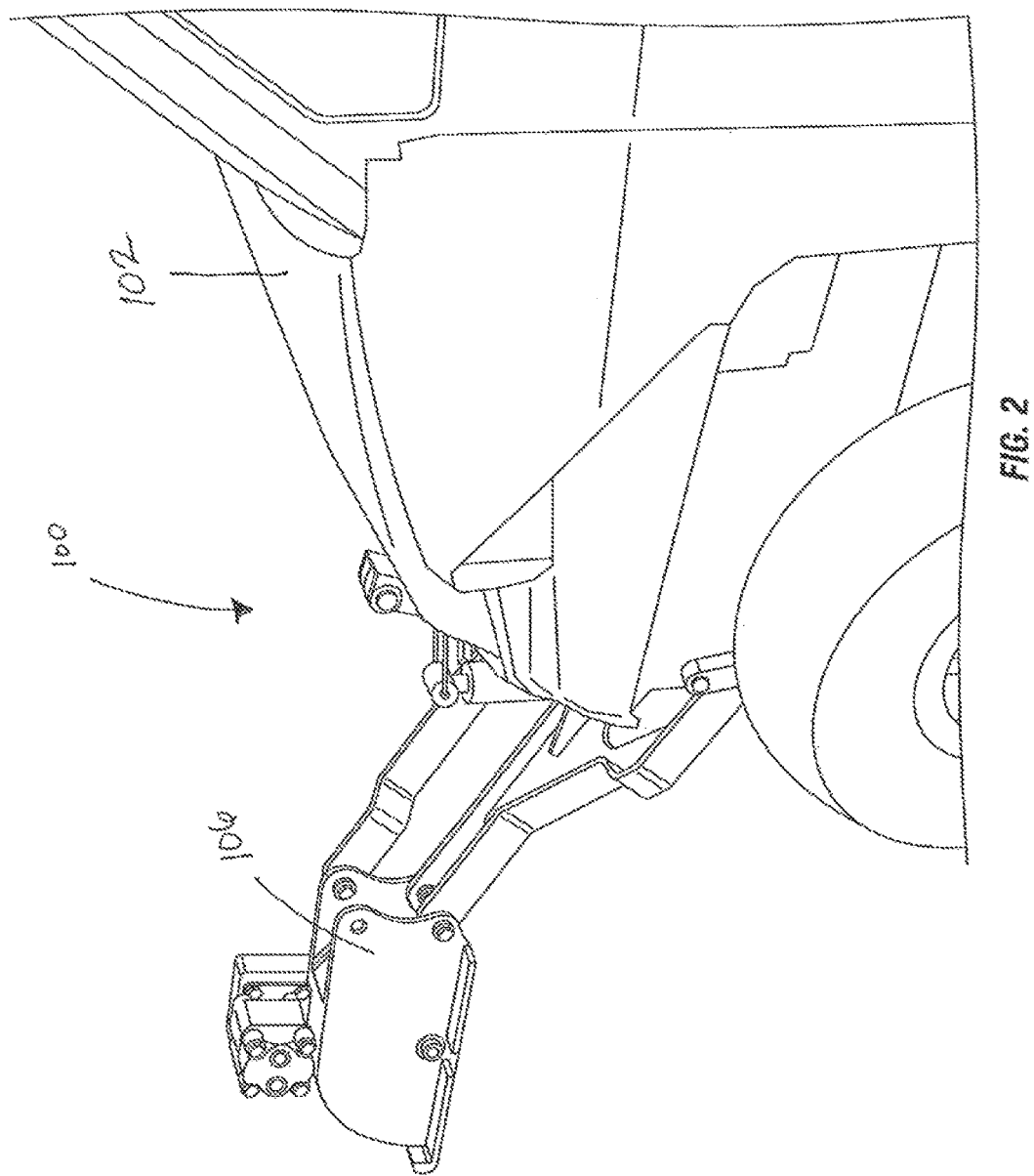
FIG. 2 is a perspective view of the components of the soil sampling collection system according to FIG. 1.
Figure 3:
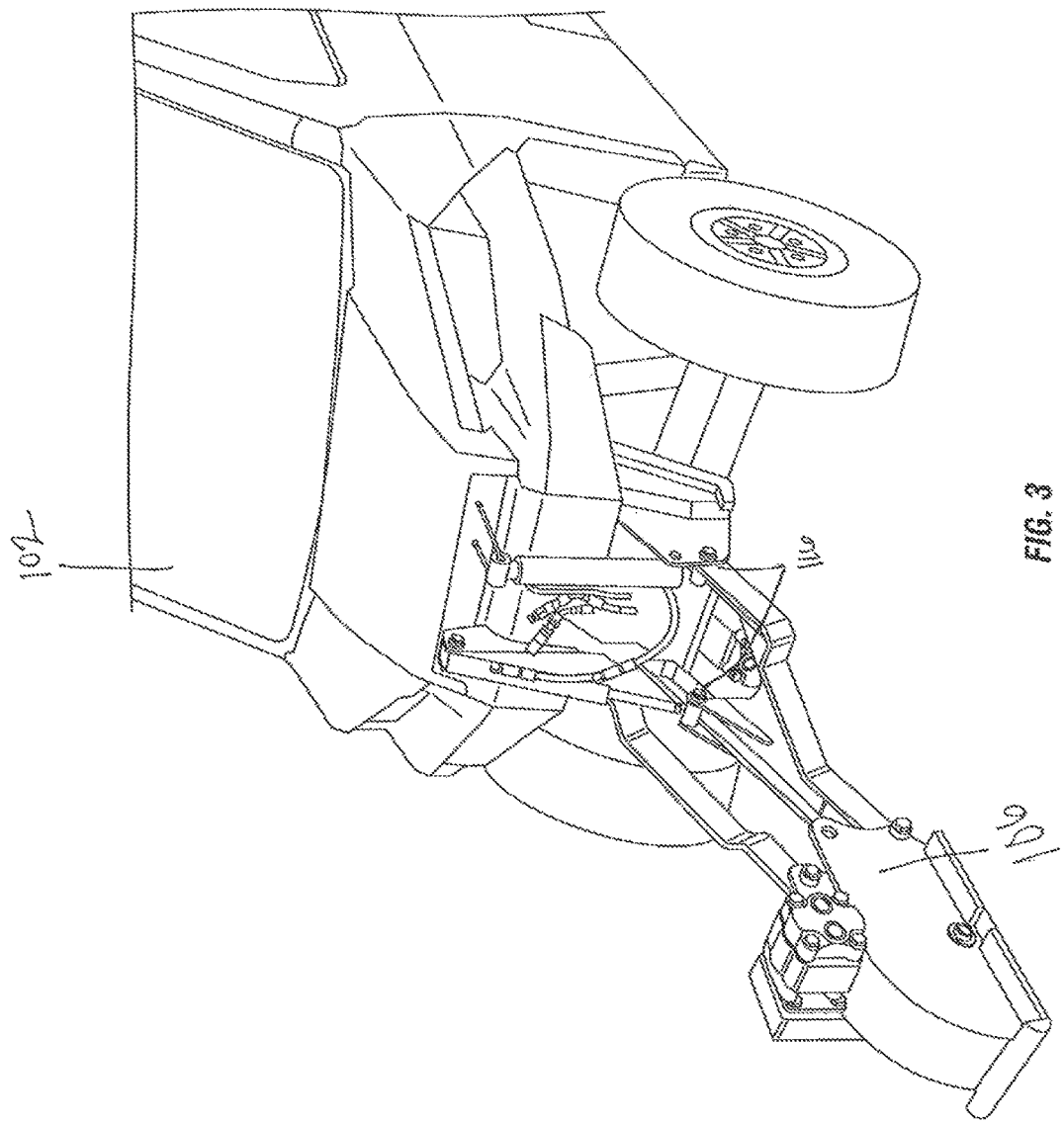
FIG. 3 is a perspective view of the components of the soil sampling collection system according to FIG. 1.
Figure 4:
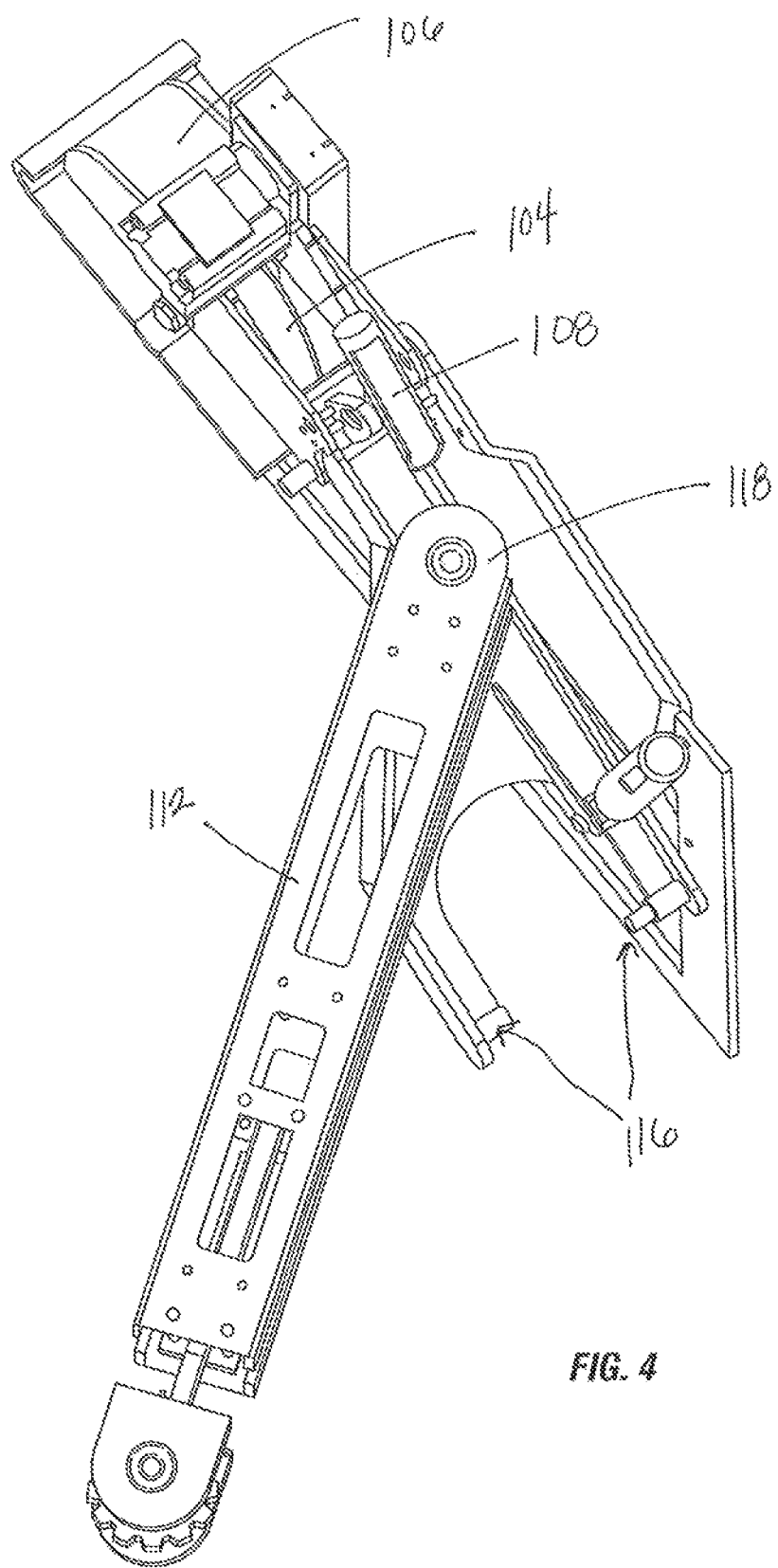
FIG. 4 is a perspective view of the components of a soil sampling collection system according to one example embodiment.
Figure 5:
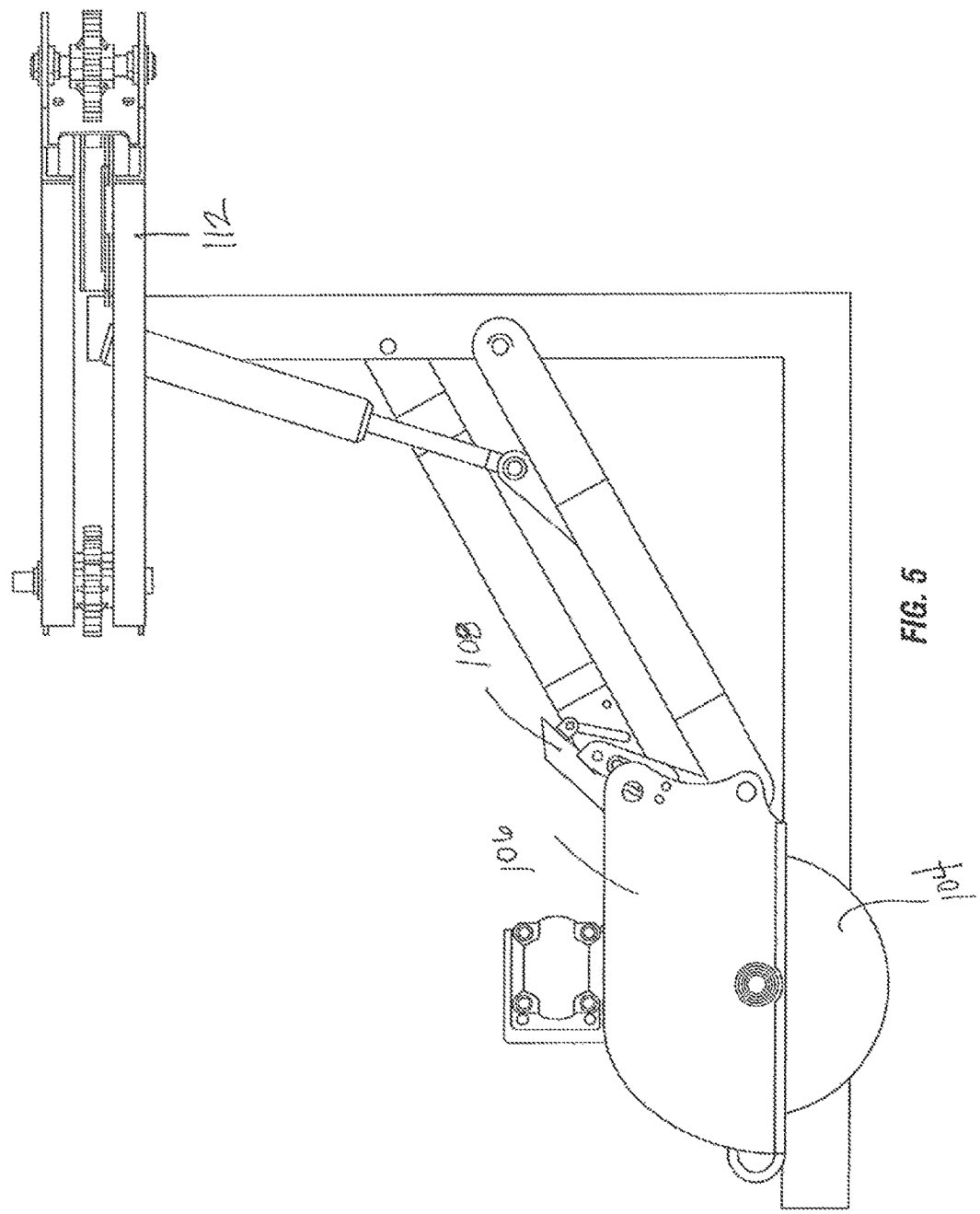
FIG. 5 is a perspective view of the components of a soil sampling collection system according to one example embodiment wherein the reservoir is in a first position.
Figure 6:
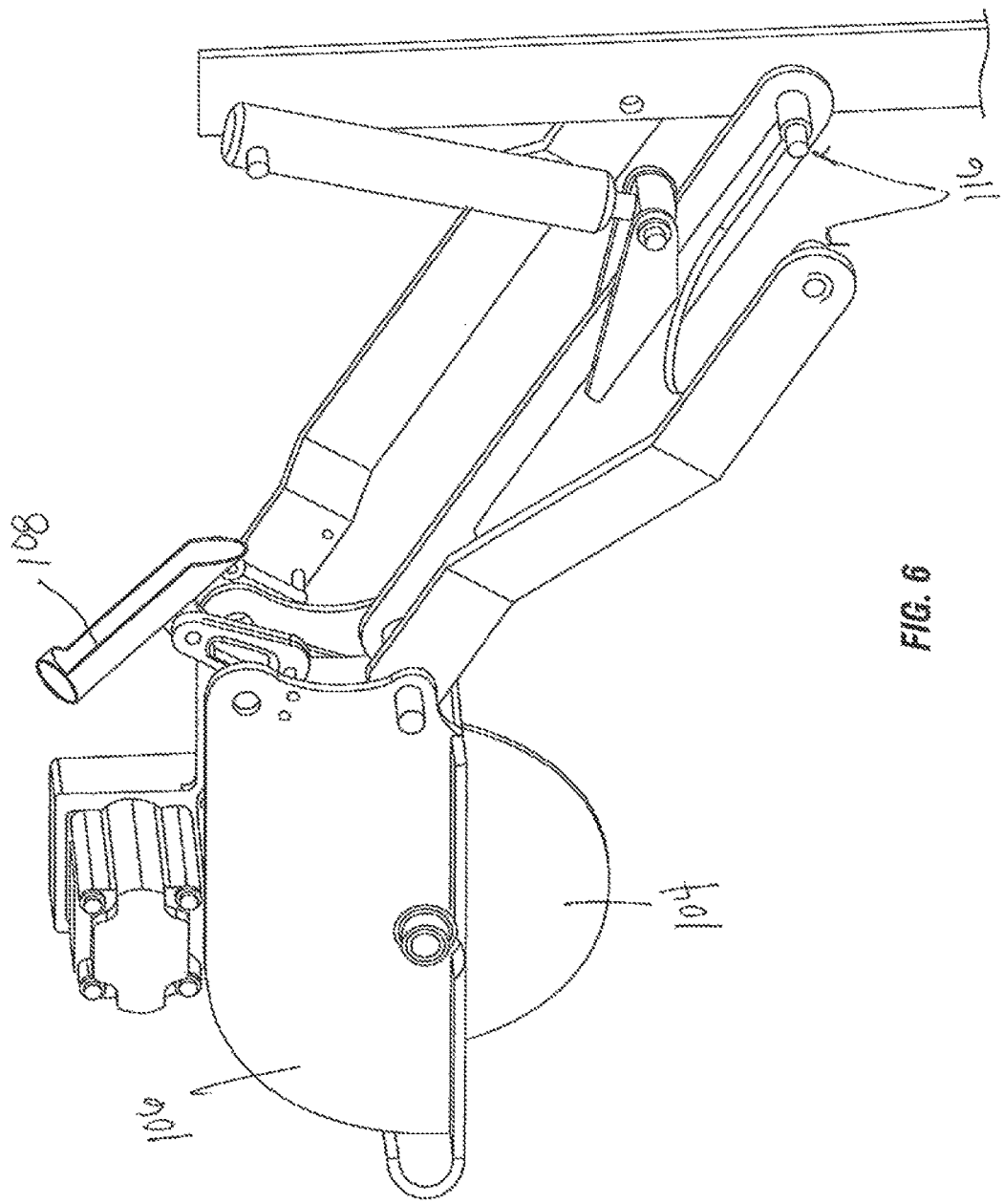
FIG. 6 depicts a perspective view of the components of a soil sampling collection system according to one example embodiment wherein the reservoir is in a second position.

In one embodiment, the blade 104 is mounted in order that when it contacts the soil, the soil travels into reservoir 108 or collection chute located in a first position (see FIG. 5). When the blade is raised, mechanics raise the reservoir 108 into a second position (see FIG. 6) which causes the reservoir 108 to transfer the soil into a soil collection bag 114.

In another example embodiment, a conveyor 112 may be mounted on the rear of the vehicle 102 cab as desired by one of skill in the art. In one embodiment, conveyor 112 may comprise twenty to thirty five soil collection bags 114, but a conveyor 112 may be designed to hold as many soil collection bags 114 as desired by one of skill in the art. Referring to FIG. 8, in a further example embodiment, a conveyor 112 may be mounted to front of the vehicle 102, wherein the conveyor 112 is mounted to receive the collected soil from the reservoir 108 and move the soil onto a conveyor 112 having a plurality of apparatuses or cups or bags into the front of the cab and into a soil sample bag 116. The conveyor automatically dumps the sample off the conveyor and into a soil sample bag.

Each soil sample collected may be geo referenced by a computer located in the cab of the utility vehicle 102 to identify the location of each of the soil samples collected.

A method to automatically and continuously collect soil samples is also disclosed. The method comprises utilizing the soil sampling collection system 100 disclosed herein. The saw blade 104 may be lowered into the ground or soil by the operator of the utility vehicle 102 or all-terrain vehicle by pushing forward on a joystick. The saw blade 104 may be controlled within the cab of the utility vehicle 102 by any other mechanism as desired by one of skill in the art. In one embodiment, when the blade 104 reaches approximately six inches deep in the ground, the soil will be thrown upward into the reservoir 108 (or collection spout) mounted on or near the saw blade guard.

Once the soil sample is in the reservoir 108, the operator of the vehicle 102 will pull back on the joystick which will raise the blade 104 up out of the ground. While the saw blade 104 is moving upwards, the reservoir 108 is tilted until the soil is automatically dumped into a soil bag, cup or apparatus 114 which may be mounted to a conveyor 112. In one embodiment, a funnel 110 may be used to assist with the transfer of the soil sample from the reservoir 108 to the soil bag 114 on the conveyor 112.

The description and illustrations are by way of example only. While the description above makes reference to various embodiments, it should be understood that many changes and modifications can be made without departing from the scope of the disclosure. Many more embodiments and implementations are possible within the scope of this invention and will be apparent to those of ordinary skill in the art. The invention is not limited to the specific details, representative embodiments, and illustrated examples in this description.

I claim:

1. A soil sampling collection system comprising:
   a. a blade mounted on a front of a utility vehicle, wherein the utility vehicle is powered to move through a designated area and configured to automatically collect soil samples as the utility vehicle moves through the designated area, wherein the blade is configured to move up and down via power hydraulics;
   b. a blade guard mounted to the blade;
   c. a soil collection reservoir mounted on or near the blade guard; and
   d. a conveyor mounted in between the soil collection reservoir and the front of the utility vehicle, wherein the conveyor comprises a plurality of soil bags configured to receive individual soil samples from the soil collection reservoir.

2. A soil sampling collection system comprising:
   a. a blade mounted on a front of a utility vehicle, wherein the utility vehicle is powered to move through a designated area and configured to automatically collect soil samples as the utility vehicle moves through the designated area, wherein the blade is configured to move up and down via power hydraulics;
   b. a blade guard mounted to the blade;
   c. a soil collection reservoir mounted on or near the blade guard; and
   d. a conveyor mounted near the soil collection reservoir and continues into the front of the utility vehicle, wherein the conveyor is configured to receive individual soil samples from the soil collection reservoir, wherein the conveyor is configured to move the soil samples at an incline on the conveyor and automatically dump the sample into a soil receiving bag.

3. A method of collecting soil samples, the method comprising the following steps: utilizing a soil sampling collection system comprising:
   (a) a blade mounted on a front of a utility vehicle, wherein the utility vehicle is powered to move through a designated area and configured to automatically collect soil samples as the utility vehicle moves through the designated area, wherein the blade is configured to move up and down via power hydraulics;
   (b) a blade guard mounted to the blade;
   (c) a soil collection reservoir mounted on or near the blade guard; and
   (d) a conveyor mounted near the soil collection reservoir and continues into the front of the utility vehicle, wherein the conveyor is configured to receive individual soil samples from the soil collection reservoir, wherein the conveyor is configured to move the soil samples at an incline on the conveyor and automatically dump the sample into a soil receiving bag; lowering the saw blade into the designated area until soil is thrown upward into the reservoir; and raising the saw blade until the reservoir is tilted causing the soil to dump onto the conveyor and travel on the conveyor until automatically dumped into a soil receiving bag.

* * * * *